(12) United States Patent
Leinsing et al.

(10) Patent No.: US 7,244,249 B2
(45) Date of Patent: Jul. 17, 2007

(54) NEEDLE-FREE MEDICAL CONNECTOR WITH EXPANDABLE VALVE MECHANISM AND METHOD OF FLUID FLOW CONTROL

(75) Inventors: Karl R. Leinsing, Hampton, NH (US); Theodore J. Mosler, Raleigh, NC (US)

(73) Assignee: Cardinal Health 303, Inc., San Diego, CA (US)

( * ) Notice: Subject to any disclaimer, the term of this patent is extended or adjusted under 35 U.S.C. 154(b) by 250 days.

(21) Appl. No.: 10/142,635

(22) Filed: May 8, 2002

(65) Prior Publication Data

US 2003/0209681 A1 Nov. 13, 2003

(51) Int. Cl.
*A61M 31/00* (2006.01)

(52) U.S. Cl. ...................... 604/500; 604/249; 604/256; 604/905

(58) Field of Classification Search ............. 251/149.1, 251/118, 149.6; 604/249, 256, 905, 246, 604/537, 538
See application file for complete search history.

(56) References Cited

U.S. PATENT DOCUMENTS

| | | | |
|---|---|---|---|
| 4,749,003 A | 6/1988 | Leason | |
| 5,122,123 A | 6/1992 | Vaillancourt | |
| 5,203,775 A | 4/1993 | Frank et al. | |
| 5,242,432 A | 9/1993 | DeFrank | |
| 5,353,837 A | 10/1994 | Faust | |
| 5,360,413 A | 11/1994 | Leason et al. | |
| 5,439,451 A | 8/1995 | Collinson et al. | |
| 5,474,544 A * | 12/1995 | Lynn | ............................ 604/537 |
| 5,509,433 A | 4/1996 | Paradis | |
| 5,549,577 A * | 8/1996 | Siegel et al. | ................. 604/256 |
| 5,616,129 A | 4/1997 | Mayer | |
| 5,616,130 A | 4/1997 | Mayer | |
| 5,676,346 A | 10/1997 | Leinsing | |
| 5,685,866 A | 11/1997 | Lopez | |
| 5,699,821 A | 12/1997 | Paradis | |
| 5,820,601 A | 10/1998 | Mayer | |
| 5,836,923 A | 11/1998 | Mayer | |
| 5,839,715 A * | 11/1998 | Leinsing | ................... 251/149.1 |
| 6,029,946 A | 2/2000 | Doyle | |
| 6,048,335 A | 4/2000 | Mayer | |
| 6,050,978 A * | 4/2000 | Orr et al. | ..................... 604/249 |
| 6,063,062 A | 5/2000 | Paradis | |
| 6,079,432 A * | 6/2000 | Paradis | ........................... 137/1 |

(Continued)

FOREIGN PATENT DOCUMENTS

EP 0 328 421 A2 8/1989

(Continued)

*Primary Examiner*—Loan H. Thanh
(74) *Attorney, Agent, or Firm*—McDermott Will & Emery

(57) ABSTRACT

A needle-free medical connector includes a housing with a first port and a second port. The connector also includes a piston element defining a fluid passageway between the first and second ports. The piston element is movable between flow and non-flow positions. The piston element has an expandable section having a variable inner width and volume that forms a part of the flow path through the connector. As the piston is compressed to the flow position, the expandable section is expanded in width by movement over a flow post thereby maintaining or increasing the volume of the fluid passageway through the connector. The expandable section has a configuration permitting the continuous flow of fluid through its entirety.

54 Claims, 11 Drawing Sheets

U.S. PATENT DOCUMENTS

| | | |
|---|---|---|
| 6,152,900 A | 11/2000 | Mayer |
| 6,183,448 B1 | 2/2001 | Mayer |
| 6,206,861 B1 * | 3/2001 | Mayer .................. 604/246 |
| 6,245,048 B1 | 6/2001 | Fangrow, Jr. et al. |
| 6,428,520 B1 * | 8/2002 | Lopez et al. ............ 604/249 |
| 6,706,022 B1 * | 3/2004 | Leinsing et al. ......... 604/247 |
| 2001/0045539 A1 | 11/2001 | Doyle .................... 251/149.1 |
| 2003/0093061 A1 * | 5/2003 | Ganem .................. 604/533 |
| 2003/0098430 A1 * | 5/2003 | Leinsing et al. ......... 251/149.6 |

FOREIGN PATENT DOCUMENTS

| | | |
|---|---|---|
| WO | WO 98-50106 | 11/1998 |
| WO | WO 01/07102 * | 2/2001 |
| WO | WO 01/07102 A2 | 2/2001 |
| WO | WO 03/047681 A1 | 6/2003 |

* cited by examiner

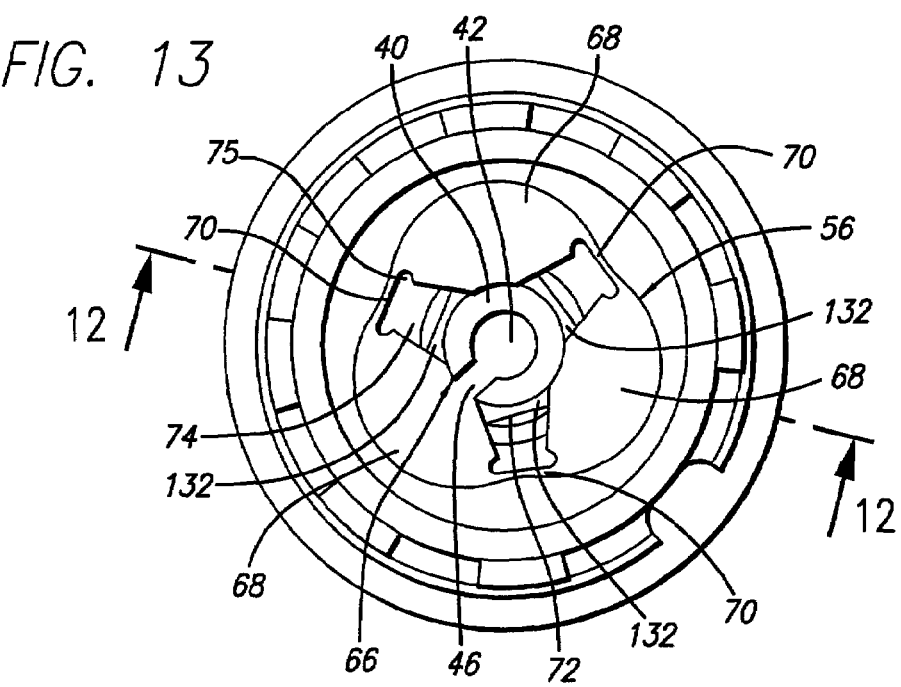
FIG. 13
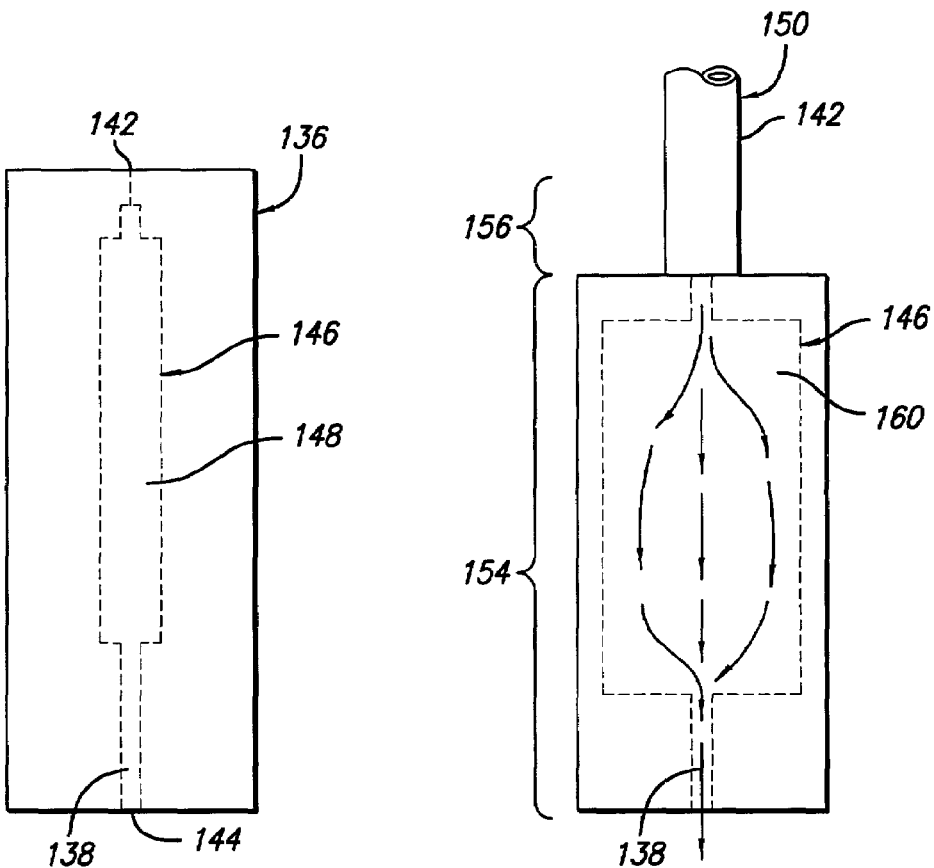
FIG. 14
FIG. 15

NEEDLE-FREE MEDICAL CONNECTOR WITH EXPANDABLE VALVE MECHANISM AND METHOD OF FLUID FLOW CONTROL

INCORPORATION BY REFERENCE

We hereby incorporate by reference U.S. Pat. No. 5,676,346 to Leinsing.

BACKGROUND

The invention relates generally to medical connectors of the type used in the handling and administration of parenteral fluids, and more particularly, to a needle-free connector employing a valve mechanism that compensates for negative fluid displacement, i.e., drawing fluid into the connector, as the connector returns to its unaccessed state from an accessed state.

Within this specification the terms, "negative-bolus effect," "positive-bolus effect," and "no-bolus effect" are used to describe the operating characteristics of medical connectors as the connector returns to its unaccessed state from an accessed state. "Negative-bolus" effect describes the condition during which fluid is drawn into the connector as the connector returns to its unaccessed state from an accessed state. "Positive-bolus effect" describes the condition during which fluid is expelled out of the connector as the connector returns to its unaccessed state from an accessed state. "No-bolus effect" describes the condition during which fluid displacement is neutralized and fluid is neither drawn into nor expelled out of the connector as the connector returns to its unaccessed state from an accessed state.

Needle-free medical connectors for injecting fluid into or removing fluid from an intravenous ("IV") fluid administration set are well known and widely used. One conventional type of such a connector includes a housing having connection ports at both ends. One connection port may comprise a female Luer port sized to receive a blunt male cannula, such as a male Luer taper. The other connection port may be located opposite the first port but in some cases is located at a ninety degree or other angle to the first port, and comprises a male Luer fitting. In many cases the second port of the connector is permanently connected to IV tubing which in turn is connected to an IV catheter that communicates with a patient's venous system.

A valve is located within the connector and in most cases uses the housing of the connector as part of the valve mechanism. When the connector is accessed, the valve opens an internal fluid passageway between the first and second ports. In some connectors, the internal fluid passageway is defined by the internal boundaries of the connector housing; in other connectors it is defined by an internal cannula or hollow spike; and still in others, the internal fluid passageway is defined by a compressible tubular body that carries the valve mechanism.

Many needle-free medical connectors create fluid displacement as the connector is accessed and unaccessed. As the connector is accessed by a blunt male Luer cannula tip inserted into the inlet or first port of the connector housing, the valve mechanism is engaged. In some connectors, the blunt cannula tip penetrates a valve device to establish fluid communication with the internal fluid flow path of the connector. In other connectors, the blunt cannula tip displaces a valve device without penetrating it in order to establish fluid communication with the fluid flow path. In either case, the volumetric capacity of the fluid flow path is often reduced by the insertion of the blunt cannula when accessing the connector. Subsequently, when the blunt cannula is removed from the connector, the volumetric capacity of the fluid flow path increases. This increase in the volumetric capacity may create a partial vacuum or pressure reduction in the fluid flow path that may draw fluid into the connector from the second or downstream end of the connector. As previously mentioned, the effect of drawing fluid into the connector in this manner is referred to as a "negative-bolus" effect in that a quantity, or "bolus," of fluid is drawn into the partial vacuum or reduced pressure location within the connector.

A negative-bolus effect as the connector returns to its unaccessed state is undesirable to some medical care providers and either a neutral bolus or positive bolus effect is preferred. It is therefore desirable to arrange for a valve mechanism that either does not affect the capacity of the internal fluid passageway through the connector as the connector is returned to its unaccessed state, or that actually decreases it.

In one approach, the negative-bolus effect may be reduced or eliminated by clamping the IV tubing between the connector and the IV catheter prior to removal of the blunt cannula from the connector. This prevents the back flow of fluid through the IV catheter and into the connector. However this is an undesirable approach in that another device, i.e. a clamp, is necessary and the care provider must remember to engage the clamp with the tubing. Furthermore, the use of additional devices adds expense and causes inconvenience in that they may not be available at the time needed. Additional steps are also undesirable in that most care providers are very busy already and would, therefore, naturally prefer to reduce the number of steps in providing effective care to patients rather than increase the number.

In another approach, one that disadvantageously also increases the number of steps in the administration of medical fluids, the operator continually injects fluid into the connector from the male device while the male device is being disengaged from the connector. By continuously adding fluid the operator attempts to fill the increasing fluid volume of the fluid flow path through the connector as the male Luer is being withdrawn, thereby reducing the likelihood of a partial vacuum and thus the likelihood of a negative bolus forming in the fluid flow path. However, this approach is also undesirable in that not only does it add a step but may require some skill in successfully carrying out the procedure.

The negative-bolus effect may also be reduced by the design of the medical connector. As previously mentioned, some medical connectors include an internal cannula or hollow spike housed inside the connector body. The internal cannula or spike is positioned to force open a septum upon depression of the septum onto the internal cannula or spike by a blunt cannula. The internal cannula or spike has an orifice at the top and, upon depression of the septum over the internal cannula or spike, the internal cannula or spike is put directly into fluid communication with the blunt cannula. The internal cannula or spike provides a generally fixed-volume fluid-flow path through the connector. Thus, as the septum returns to its closed position the partial vacuum formed within the connector, if any, is not as large as the partial vacuum formed in a connector having a more volumetrically variable internal fluid passageway. A disadvantage of typical connectors having an internal cannula or spike is a lower fluid-flow rate caused by the small lumen in the cannula or spike. Additionally, it has been noted that with the connector design having a fixedly-mounted internal spike and a movable septum that is pierced by that spike to permit fluid flow, such pierced septum may be damaged with multiple uses and a leaking connector may result.

Another connector provides a valve mechanism that includes a flexible body within which is located a relatively rigid leaf spring. The housing of the connector includes an internal cannula and upon depression of the flexible body by the introduction of a blunt cannula through a port, the internal cannula forces the leaves of the leaf spring apart. The leaves in turn force the top of the flexible body apart and open a slit contained therein. The opening of the slit establishes fluid communication between the accessing blunt cannula and the lumen of the internal cannula. The flexible body also creates a reservoir-type area between the flexible body and the outer wall of the internal cannula in which fluid is retained. Fluid flows into the reservoir initially and is retained there until the valve returns to the unaccessed state. As the external blunt cannula is removed from the connector, the leaf spring and reservoir collapse and fluid is forced out of the reservoir and into the internal cannula lumen.

This positive displacement of fluid may result in a positive bolus effect as the valve returns to its unaccessed state. However, the valve mechanism is relatively complex with a leaf spring being incorporated into a flexible member which adds some manufacturing concerns as well as at least one additional part; i.e., the leaf spring. Manufacturing concerns and additional parts can tend to cause expenses to rise, an undesirable effect in the health care industry today where manufacturers strive to provide effective products at lower costs. Further, the reservoir-type system does not permit continuous flow through the entire expandable flexible body section. Instead, fluid flows into the reservoir, is retained, and once the reservoir is filled, fluid no longer flows into it.

Hence, those concerned with the development of medical connectors have recognized the need for a medical connector having a valve mechanism that avoids the negative-bolus effect by producing either a positive-bolus effect or a nobolus effect. The need for a medical connector that provides these effects without sacrificing fluid-flow rate or structural simplicity has also been recognized. Further needs have also been recognized for a medical connector that is less expensive to manufacture, that is efficient in operation, and that includes fewer parts. The present invention fulfills these needs and others.

SUMMARY OF THE INVENTION

Briefly, and in general terms, the invention is directed to a medical connector having a valve mechanism, the connector providing a positive-bolus effect or a no-bolus effect upon the connector returning to the unaccessed state from an accessed state.

More particularly, the invention is directed to a connector for controlling the flow of fluid, the connector having an internal fluid passageway by which fluid may flow through the connector, the connector comprising a housing having a first port and a second port, the first port being adapted to receive a blunt cannula and the second port adapted for fluid communication with a fluid conduit and a movable element positioned within the housing, the movable element having a first position at which the movable element blocks fluid flow through the housing and a second position at which the movable element permits fluid flow through the housing, the movable element comprising a head defining a bore forming a part of the fluid passageway, the head configured to urge the bore to open such that when the movable element is in the second position, the bore self-opens to permit fluid flow, the bore adapted to close when the movable element is in the first position; and an expandable section defining an inner conduit, the inner conduit forming a part of the fluid passageway through the connector, the expandable section configured so as to urge the inner conduit to have a first width and a flow post that is disposed within the housing and is adapted so that when the movable element is at the second position, the flow post extends into the inner conduit and expands the size of the inner conduit to a second width, the second width being larger than the first width.

In another aspect, the first and second widths of the inner conduit of the expandable section are selected such that the fluid passageway has a first volume when the movable element is in the first position and a second volume when the movable element is in the second position, the second volume being larger than the first volume. In a related aspect, the first and second widths of the inner conduit of the expandable section are selected such that the fluid passageway has a first volume when the movable element is in the first position and a second volume when the movable element is in the second position, the second volume being approximately the same as or larger than the first volume.

In more detailed aspects of the invention, the inner conduit of the expandable section is configured such that fluid may continuously flow through the entire inner conduit when the movable element is located in the second position. Yet further, the connector further comprises a flow post having opposing ends, the flow post defining a lumen extending between the opposing ends, one end being in fluid communication with the second port and the lumen forming a part of the internal fluid passageway through the connector. The flow post comprises a wall, the wall defining a slot providing a fluid path between the exterior of the tube and the lumen. The flow post is configured in relation to the moveable element such that, when the movable element is in the second position, the lumen and slot of the flow post are positioned, at least in part, within the inner conduit of the expandable section such that fluid may flow through the inner conduit of the expandable section, through the slot, through the lumen of the flow post, and through the second port of the housing.

In a related aspect, the inner conduit of the expandable section has opposing first and second ends, the first end being adjacent the bore of the head and the movable element defines an orifice located at the second end of the inner conduit, the orifice forming part of a flow path extending from the bore, through the inner conduit, and out of the inner conduit through the orifice. The lumen and slot of the flow post extend, at least in part, to a location outside the inner conduit of the expandable section when the movable element is at the second position and the flow path further extends from the orifice, through the slot, and into the lumen at the location outside of the inner conduit.

In yet other aspects according to the invention, the moveable element further comprises a spring section connected to the expandable section and the flow path further extends from the orifice, and into the spring section. The housing includes a narrowed region adjacent the first port, the head of the movable element being located in the narrowed region when the movable element is in the first position, the narrowed region being dimensioned so as to cause the bore of the head to close. Additionally, the housing includes a constricted region, the expandable section being located in the constricted region when the movable element is in the first position, the constricted region being dimensioned so as to receive the expandable section to permit the inner conduit to move to the first width.

In a more detailed aspect, the exterior of the expandable section may include longitudinal raised ridges that interact with the constricted region to compress the expandable section and decrease its internal volume further when in the first position, which has the effect of increasing the amount of positive bolus. The first width will be smaller due to the further compression caused by the raised ridges. The raised ridges may take the form of small longitudinal bumps, or other projections that will interact with the constricted region.

In other more detailed aspects, the expandable section is connected to the head and the moveable element further comprises a spring section connected to the expandable section, the spring section being adapted to urge the movable element to the first position at which the expandable section is placed within the constricted region. The expandable section, and the spring section are molded as an integral moveable element. The expandable section comprises a plurality of relatively flexible membrane elements and a plurality of relatively stiff wall elements, the membrane elements connecting together adjacent edges of the wall elements. The membrane elements are adapted to stretch outwardly to permit expansion of the inner conduit when the inner conduit has the second width.

In a further detailed aspect, the spring section of the connector includes a bore that forms a part of the connector internal fluid passageway. The spring section bore has a first volume when the spring section is uncompressed and a second volume when the spring section is compressed wherein the spring section bore second volume is greater than the spring section bore first volume.

In yet another aspect, the invention is related to a connector for medical use, adapted to facilitate the flow of fluid therethrough. The connector includes a first port, a second port, and a movable element defining a fluid path between the first port and the second port. At least one of the inlet port, the outlet port, and the movable element is formed to include an antimicrobial agent.

These and other aspects and advantages of the invention will become apparent from the following detailed description and the accompanying drawings, which illustrate by way of example the features of the invention.

BRIEF DESCRIPTION OF THE DRAWINGS

FIG. 13 is a cross-sectional view of the enlarged details of FIG. 11 showing the self-collapsing inner conduit at its second width, the flow post, the slot in the flow post, and showing in particular orifices existing at the base of the inner conduit that permit fluid flow from all parts of the inner conduit into the slot of the flow post so that there is continuous fluid flow through the entire inner conduit;

FIGS. 14 and 15 are schematic depictions of an operational principle utilized by a medical connector that incorporates aspects of the present invention.

DETAILED DESCRIPTION OF PREFERRED EMBODIMENTS

Figure 1:
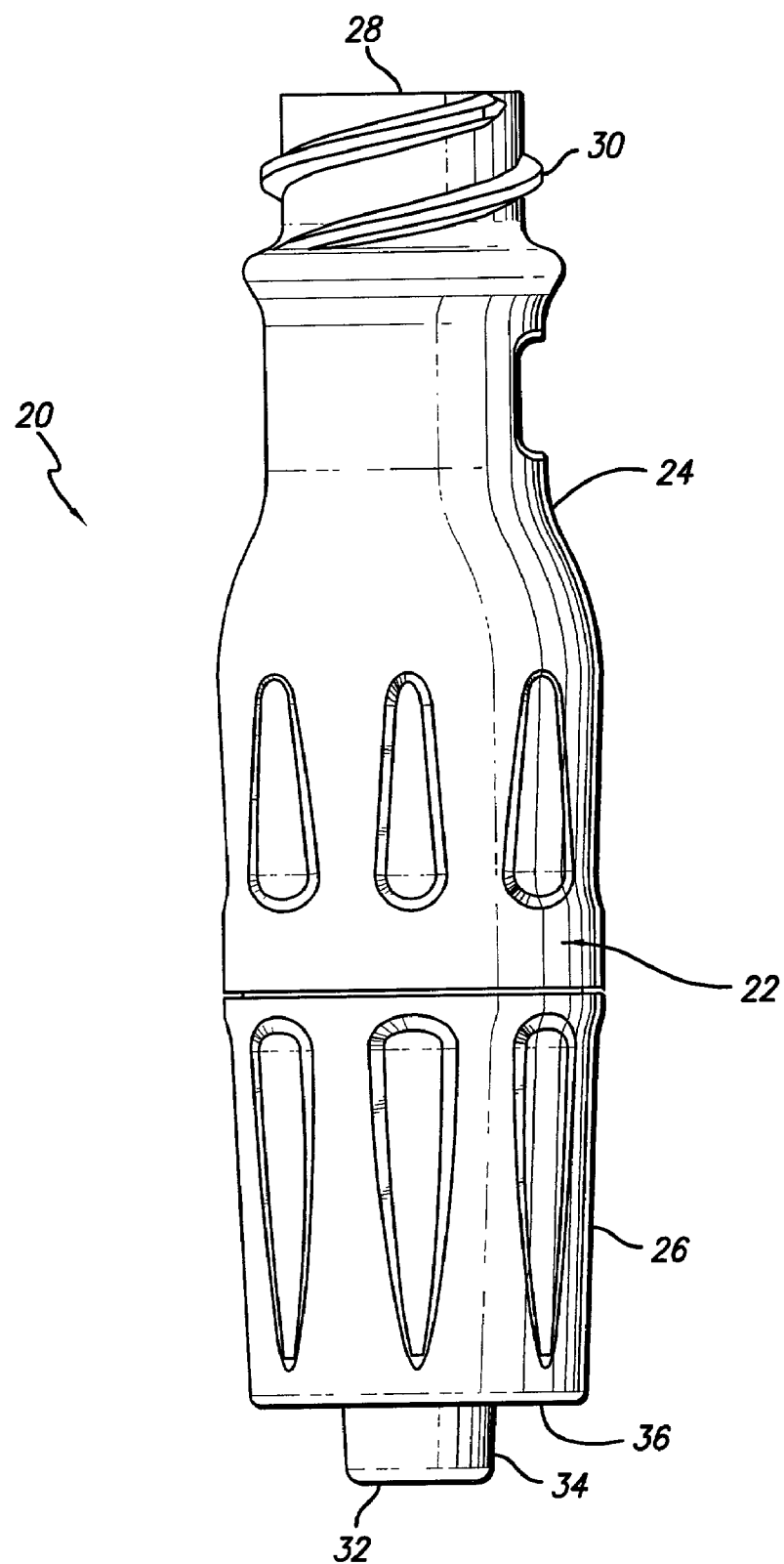
FIG. 1 is a side view of an assembled medical connector that incorporates aspects of the present invention, showing a first port surrounded by thread elements for receiving a blunt connector having a threaded cuff, and a second port comprising a blunt male connector.

Referring now in detail to the drawings in which like numerals refer to like or corresponding elements among the several figures, there is illustrated in FIG. 1 a side external view of a medical connector that includes various aspects of the present invention. The particular connector configuration exemplified in the figures is for illustration purposes only. The connector may be embodied in different configurations including, but not limited to, Y-connectors, J-loops, T-connectors, tri-connectors, slip Luers, tubing engagement devices, access pins, vial adapters, blood tube adapters, bag access pins, vented adapters, and others. The drawings are for illustration purposes only.

FIG. 1 presents an embodiment of a medical connector 20 having a housing 22 that is formed of an upper housing portion 24 and a lower housing portion 26. The upper housing portion 24 has a first port 28, that in this case is a female Luer connector port with thread elements 30 located about the exterior. The lower housing portion 26 terminates in a second port 32 that, in this case, comprises a male Luer connector 34 defining a lumen 35 (lumen not visible in FIG. 1) and with a threaded locking collar 36 (threads not visible in FIG. 1). Together, the upper housing portion 24 and the lower housing portion 26 form the connector housing 22. The housing 22 may be molded of a material containing a phosphorescent colorant to render the connector 20 visible in a darkened room or may be formed of an opaque and/or a transparent material. Identifying indicia, such as a manufacturer name or trademarks may be molded into the housing, preferably in raised letters and numbers.

Figure 2:
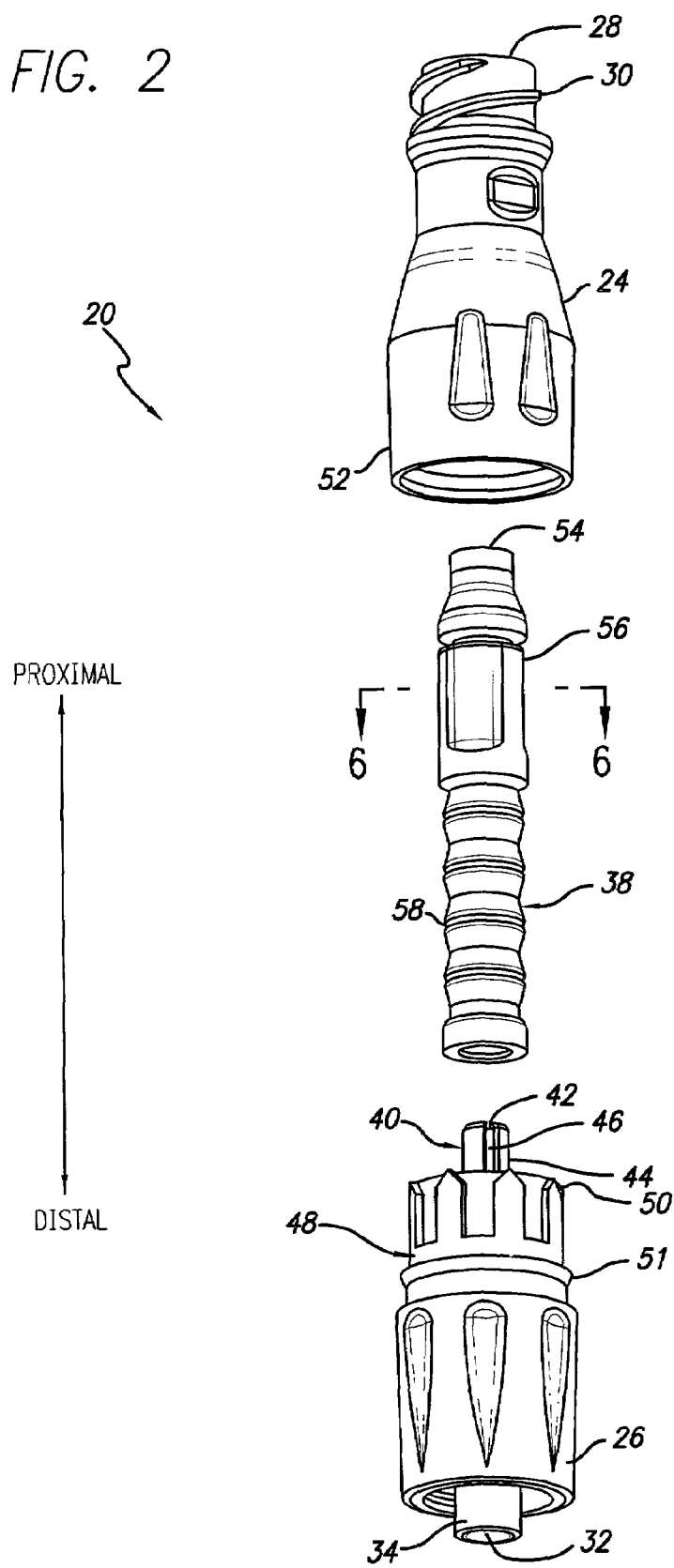
FIG. 2 is an exploded perspective view of the medical connector of FIG. 1 showing the three components of the medical connector of this embodiment, including an upper housing portion, an internal piston element, and a lower housing portion.

Turning now to FIG. 2, an exploded, somewhat perspective view of the connector 20 of FIG. 1 is shown. The connector 20 comprises three parts in this embodiment: the housing 22 (see FIG. 1 for numeral 22) that comprises the upper housing portion 24 (first part) and the lower housing portion 26 (second part). The connector 20 also includes a movable element or piston element 38 (third part). As will be described in more detail below, the piston element 38 is mounted over a flow post 40 that is formed as part of the lower housing portion 26. In one embodiment, the flow post 40 extends distally from the center of the lower housing portion 26 and has an inner lumen 42 extending the length of the flow post. In the wall 44 of the flow post, a longitudinal slot 46 is formed that may extend the length of the flow post.

The housing of the embodiment shown in FIGS. 1 and 2 includes details that aid in manufacturing and that lower the costs of manufacture. As an example, the exterior surface of the upper portion 48 of the lower housing portion 26 is molded to include a crown shaped outer shell that has several crown points 50. Although not shown in FIG. 2, the interior of the lower portion 52 of the upper housing portion 24 is molded to include a complementary shaped pattern to the crown-shaped lower housing portion. The crown shapes 50 of the lower housing portion 26 mate closely with the complementary crown shapes (not shown) of the upper housing portion 24 thereby facilitating a snap-fit assembly of the medical connector housing. The raised, snap fit, annular bump 51 formed on the lower housing 26 mates with a complementary geometry in the upper housing 24 so that the upper and lower housings may be snapped together. The geometry of the crown shapes prevents the upper housing 24 from rotating in relation to the lower housing 26 when snapped together. Because the flow path is through the piston element 38 and not around it, the disclosed snap-fit assembly does not raise concerns of fluid leakage. A vent (not shown) is added to a crown section in one embodiment to reduce any partial vacuum that may have otherwise developed inside the housing and that may have affected the return of the piston to the unaccessed position.

Permanent assembly may also be achieved by means such as ultrasonic weld, a spin weld, bonding, or by other means in other embodiments. This disclosed snap-fit design has been found to result in an efficiently manufactured housing assembly that is accurately assembled, that is quickly and efficiently snapped into a secure assembly.

Figure 3:
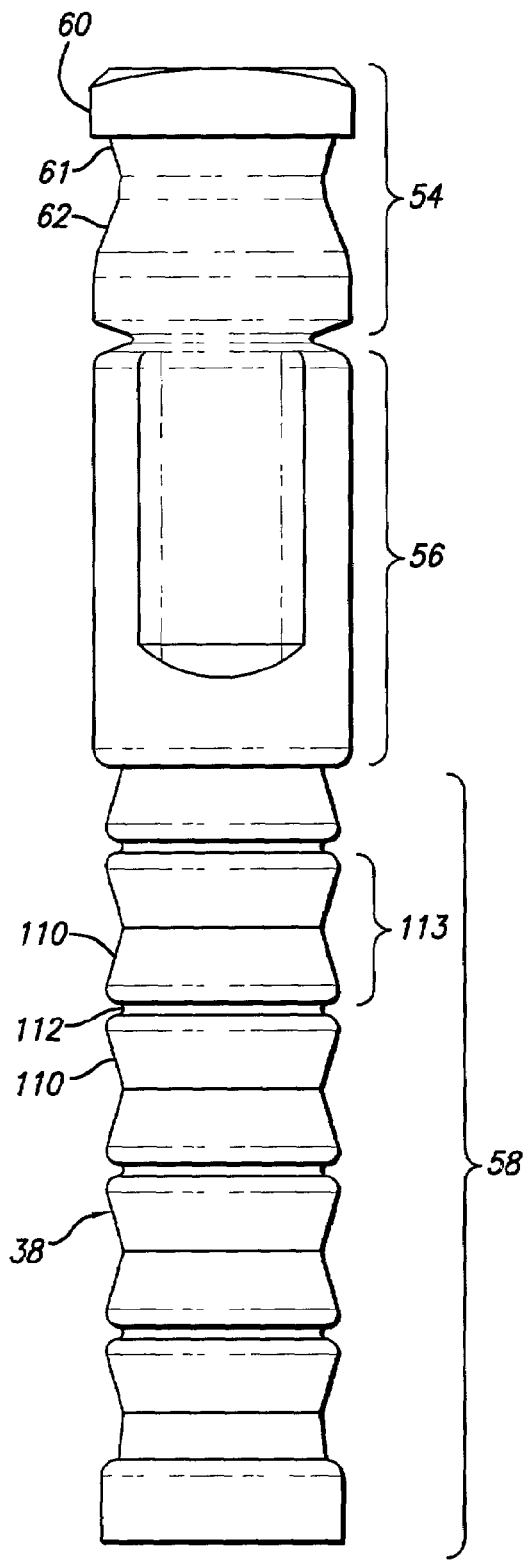
FIGS. 3 and 4 are elevational views, at right angles to each other, of the piston element shown in FIG. 2.
Figure 4:
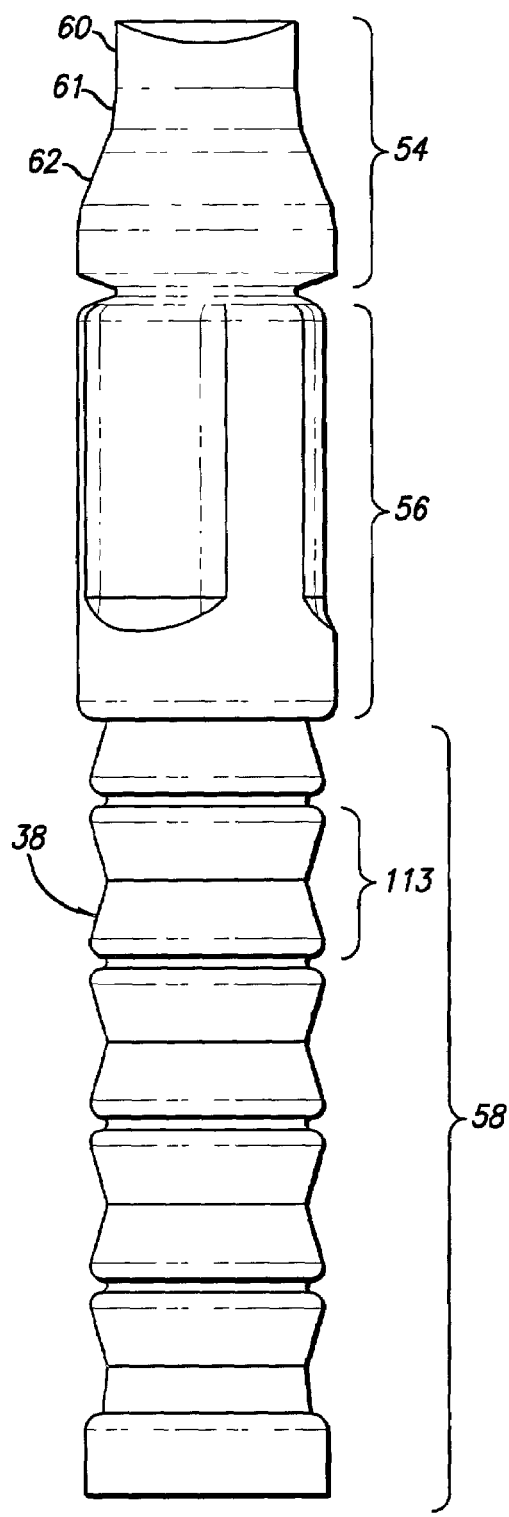

Referring now to FIGS. 3 and 4 enlarged views of a resiliently deformable piston element 38 are presented. The same piston element 38 is shown in both views, each rotated at right angles to the other. The piston element includes three main sections; a piston head 54, an expandable section 56, and a spring section 58. The expandable section is located between the head and the spring section.

The piston element may suitably be molded as one piece from a resilient material such as silicone or rubber.

Figure 5:
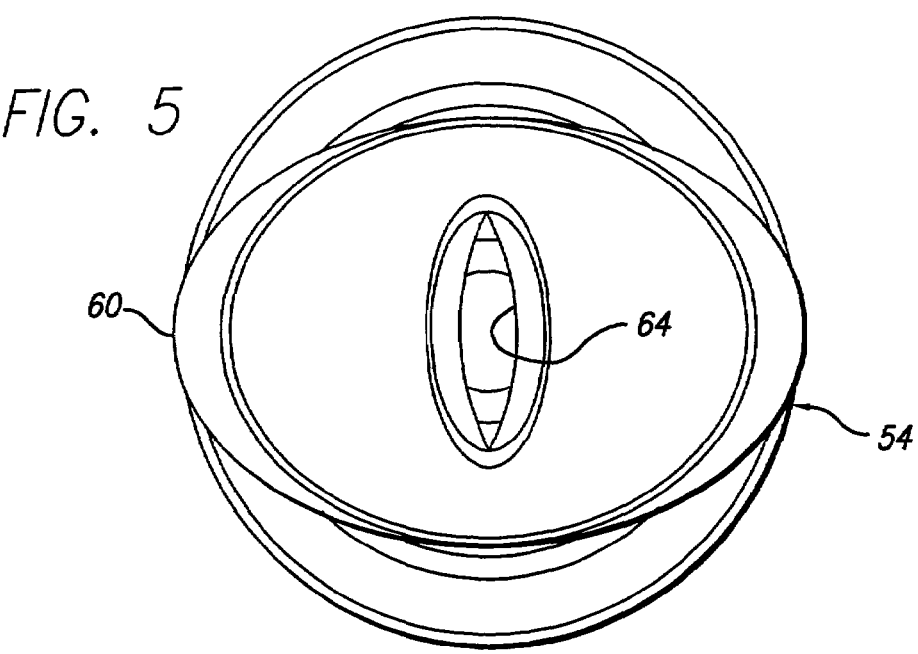
FIG. 5 is an end view of the self-opening head of the piston element of FIG. 3 showing its normally-open marquise-shaped bore.

The piston head 54 includes a top portion 60 that is elliptical in outer shape, and a bottom, tapered shoulder section 62 that is circular in plan cross-section. Connecting the two is an elliptical-conical section 61. Referring now also to FIG. 5, a marquise-shaped bore 64 is formed in the elliptically-shaped top section 60. For further details on the operation of the piston head, see U.S. Pat. No. 5,676,346 to Leinsing, which is incorporated herein by reference. Although not shown in FIGS. 3, 4, or 5, the expandable section 56 includes a deformable inner conduit 66 that forms one of the aspects of the invention.

The piston element 38 in this embodiment may include an antimicrobial agent. The agent may be included in the material forming the piston element or may be added to the outer surface of the piston element as a coating. These agents reduce the incidence of infection if the connector is not properly disinfected with an alcohol wipe prior to use. The upper housing portion 24, in particular the first port 28, the lower housing portion 26, in particular the flow post 40 and male Luer connector 34 defining the lumen 35 and forming a second port 32 (FIG. 7), may also include an antimicrobial agent. These surfaces comprise the flow path through the connector 20, in addition to flow through the piston element 38. The peripheral surface of the piston element 38 is also lubricated with silicone oil to facilitate movement of the piston element within the connector. The antimicrobial agent may be chosen from materials consisting of silver, silver oxide, and silver sulfadiazine, as well as other materials.

Figure 6:
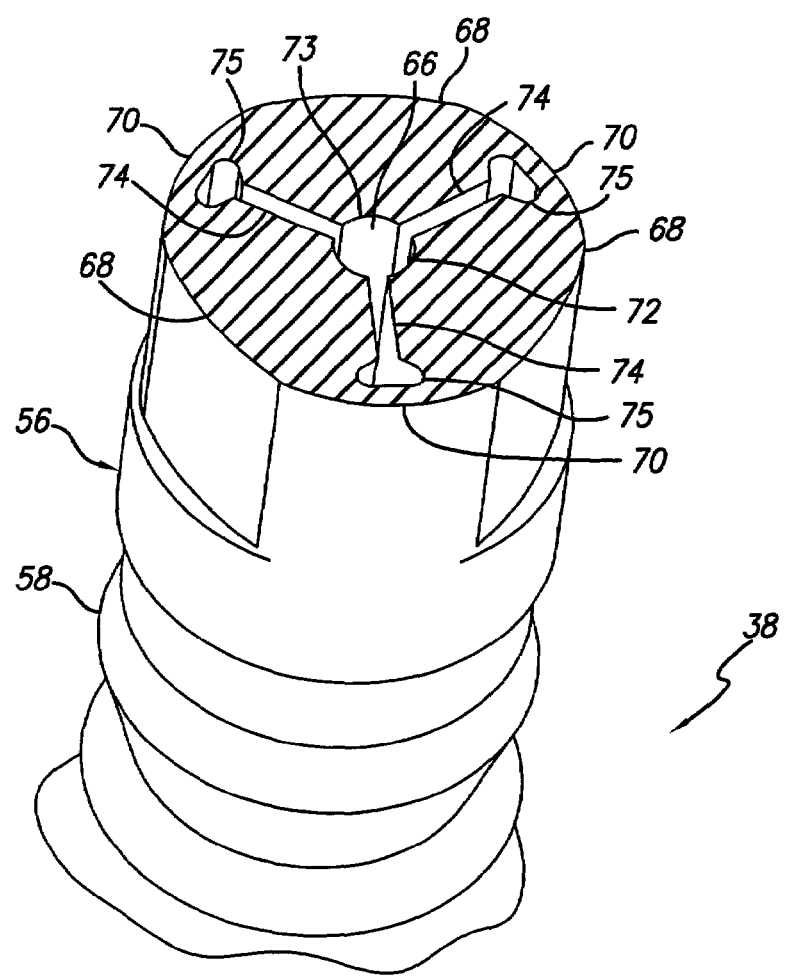
FIG. 6 is a perspective view in partial cross section of the piston element of FIG. 2 with the section taken across the line marked 6—6, showing the inner conduit of the expandable section in its relaxed condition.

Referring now to FIG. 6, a perspective cross-sectional view of the expandable section 56 is shown. The expandable section includes an inner conduit 66 defined by a plurality of opposing relatively stiff wall elements 68 that are connected together by opposing relatively flexible membrane elements 70. The interconnection of the stiffer wall elements 68 by the flexible membrane elements 70 defines the inner conduit 66 that has a diameter 72. In the disclosed embodiment, the sectional shape of the inner conduit, viewed from the top, resembles a central circular hub 73 from which spokes 74 radiate outwardly. Each spoke terminates in an enlarged circular slot 75. It should be noted that the terms "width" or "diameter" are not used herein in a restrictive sense; that is, they are not used to indicate the dimension in any particular direction within the inner conduit. They are used instead in a general sense to indicate the interior cross-sectional opening size of the inner conduit measured at right angles to the longitudinal axis 76 (FIG. 7) of the moveable element 38.

As will be discussed and shown in greater detail below, the flexible membrane elements 70 are adapted to stretch so as to permit the width 72 of the inner conduit 66 to increase when a radially expansive force is applied from the center of the expandable section 56. Due to the relative stiffness of the stiffer wall elements 68, the length of the inner conduit 66 remains substantially constant under such radially expansive force. When the radially expansive force is removed or reduced, the inner conduit 66 is self-collapsing and tends to collapse until it reaches its first width, as shown in FIG. 6, under the force provided by the resilient material of the expandable section 56.

It can be noted that the inner conduit 66 shown in FIG. 6 has an unusual opening shape. However, the advantageous nature of this opening shape will be apparent when later figures are discussed below.

Figure 6A:
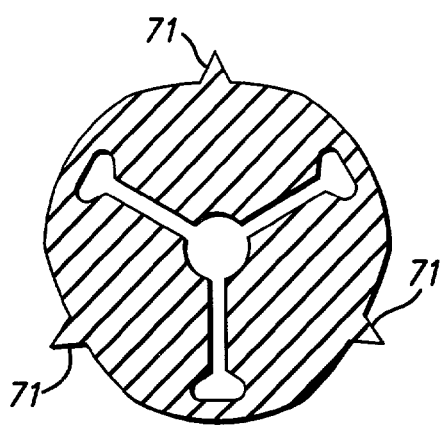
FIGS. 6A and 6B present views of the expandable section having external ridges to result in compression of the expandable section when in the first position within the housing of the connector.
Figure 6B:
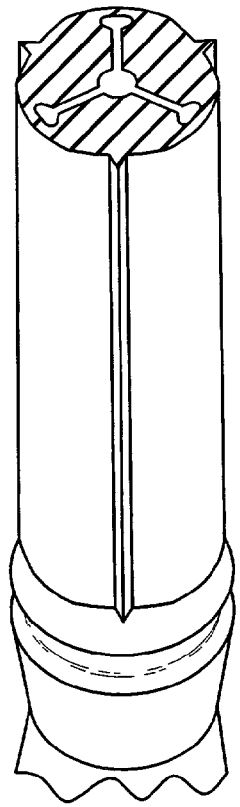

Briefly referring now to FIGS. 6A and 6B, the longitudinal ribs 71 may be formed on the exterior of the expandable section 56 to assist in further compressing the expandable section 56 when it is moved to an unaccessed position, as shown and described below in FIG. 7. This further compression of the expandable section 56 will further reduce the internal volume when the piston is in the first position, again as will be described in more detail below. The exact configuration of the longitudinal ribs 71 may vary and the shape shown in FIGS. 6A and 6B is exemplary only. They may take the form of raised bumps or other shapes. They may not extend for the entire length of the expandable section but may be located over only a portion of it. Other variations are possible.

Figure 7:
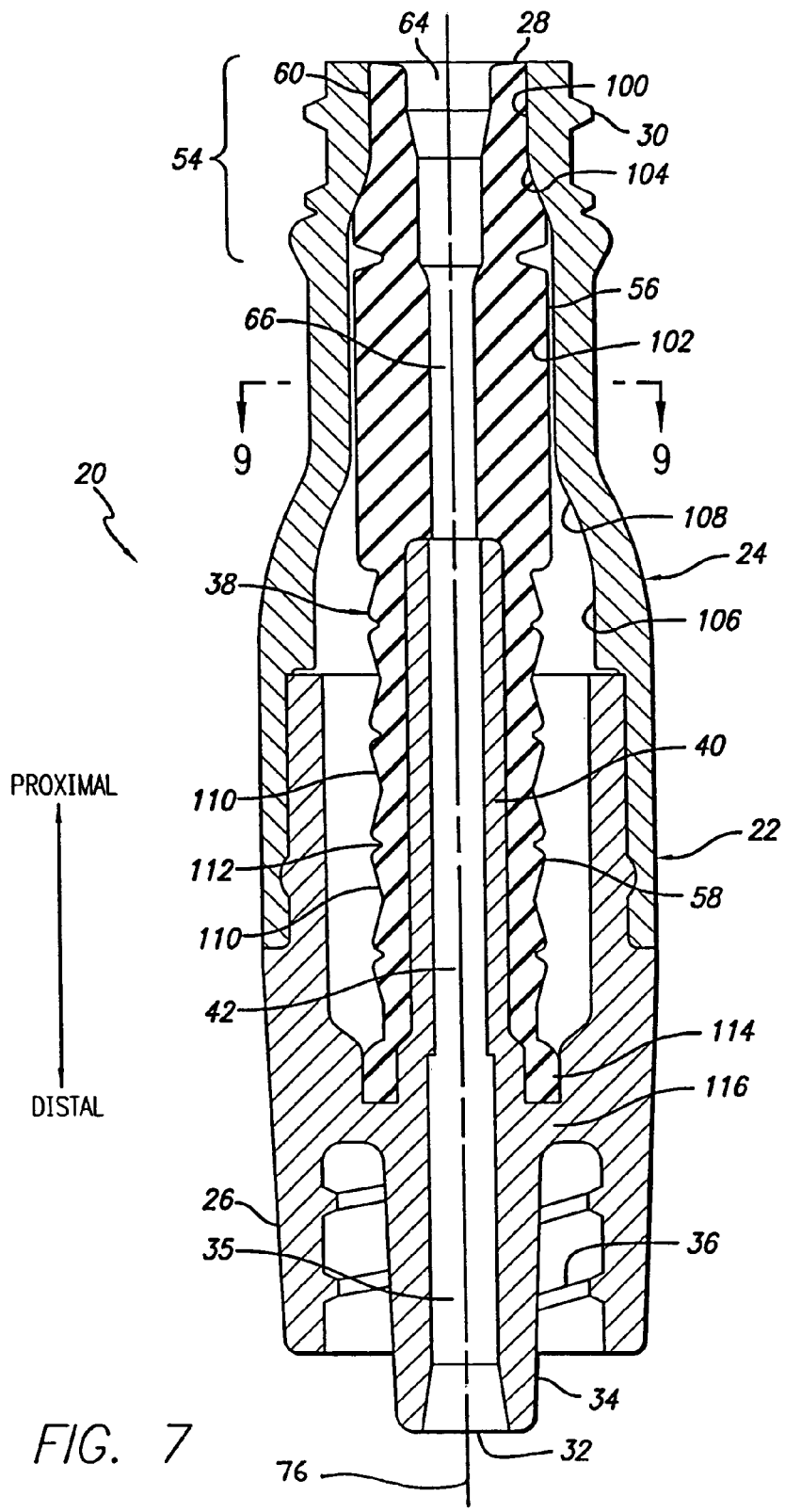
FIG. 7 is a sectional elevation of the medical connector of FIG. 1, showing the connector in a non-accessed state with the piston element in its first position in which the self-opening bore of the piston head is closed to fluid flow by the narrowed first port of the housing and the expandable section has been allowed to return to its first, as-molded width within the constricted region of the housing.

Referring now to FIG. 7, the connector 20 of FIG. 1 is shown in vertical cross-sectional format. It should be noted that the connector depicted in FIG. 7 is in an unaccessed state. That is, no blunt cannula has been inserted into its first port 28 for fluid communication through the connector.

The upper housing portion 24 has sections of varying internal diameter.

The internal section directly adjacent the first port 28 includes a standard ANSI/ISO Luer taper portion 100 that incorporates a very slight inward taper. The center portion 102 has a larger internal diameter than the Luer taper portion 100 and is separated from the Luer taper portion 100 by a tapered lock portion 104. The bottom portion 106 of the upper housing portion 24 has a larger internal diameter than the center portion 102 and is separated from the center portion by a tapered ramp portion 108. Thus, in relation to the bottom portion 106, the center portion 102 represents a constricted region, and, in relation to the center portion 102, the Luer taper portion 100 represents a narrowed region. The bottom portion 106 has an inner diameter large enough to permit the inner conduit 66 to be expanded from its first as-molded width to a second larger expanded width when the expandable section 56 is positioned within the bottom portion.

Referring now to both FIGS. 7 and 3, the spring section 58 is shown and will be discussed in more detail. In the embodiment shown, the spring section 58 is configured to include a plurality of relatively stiff annular wall portions 110 (only two of which are indicated by the numeral 110 to preserve clarity in the drawings), connected to each other by relatively flexible annular hinges 112, together forming the spring section. The annular wall portions 110 disposed at the center of the spring section have an hourglass shape 113 (see FIG. 3) that permits their bending at the center point. The hourglass shape and the hinges result in compression of the spring 58 in a controlled elastic fashion to assume a bellows-like shape in response to an axially compressive force, as will be described in relation to FIG. 10 below.

Figure 10:
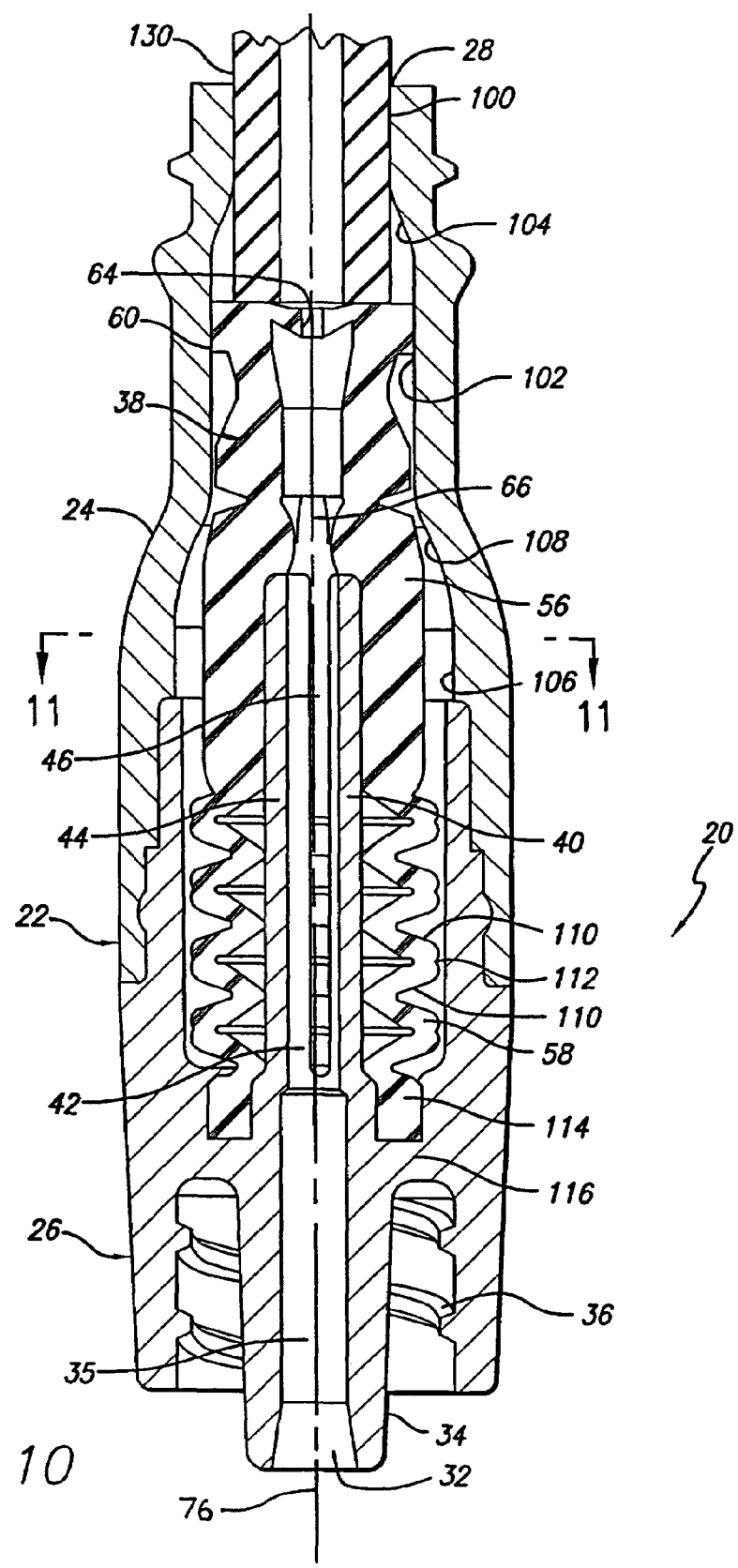
FIG. 10 is a sectional elevation of the medical connector of FIG. 1, showing the connector in an accessed state with the piston element having been moved to its second position in which the self-opening bore of the piston head has self-opened to fluid flow and the inner conduit of the expandable section has expanded to its second width for increased internal volume.

The inner diameter of the spring section 58 is selected to allow positioning of the spring over the flow post 40 and the outer diameter of the spring is selected to allow positioning of the spring within the housing 22 and to control the desired spring force. The spring is easily slidable over the flow post 40 in the embodiment shown but when a compressive force is applied to the spring, the flow post prevents the spring from buckling and assists the spring in a controlled change to a bellows-type shape. The flow post 40 acts as a guide to the spring in that it guides it to the correct position within the housing 22 in general and it guides it to a properly formed compressed or bellow-type configuration thereby preventing it from buckling when a compressive force is applied to it. Additionally, the flow post 40 is located within the flow path and therefore consumes some volume in that flow path resulting in a desirable lower priming volume through the connector 20. Because the flow post takes up some volume in the flow path, there is a smaller dynamic volume change between the unaccessed and accessed configurations of the connector 20 (FIG. 7 and FIG. 10). Consequently, the possible positive and negative boluses will be smaller. It should be noted that in other embodiments, the flow post 40 can vary in shape. It may be made thicker, thinner, shorter, and have other shapes beyond what are shown in the drawings.

In the unaccessed state of the connector 20 as shown in FIG. 7, the spring section 58 of the piston element 38 urges the expandable section 56 through the ramp portion 108 of the upper housing portion 24 into the relatively constricted center portion 102. The location of the expandable section 56 in this constricted location allows the expandable section to assume its as-molded condition and to fit loosely, in this embodiment, within the upper housing, as shown in FIG. 7, with the inner conduit 66 having the first as-molded width. However, referring back to FIGS. 6A and 6B, the exterior of the expandable section 56 may have the raised ridges 71 that will interfere with the constricted center portion 102 of the housing thereby causing the expandable section 56 to be compressed (not shown). The spring force must be large enough to force the expandable section 56 completely into the constricted portion 102 overcoming the interference between the ribs and the inner wall of the constricted section.

Figure 9:
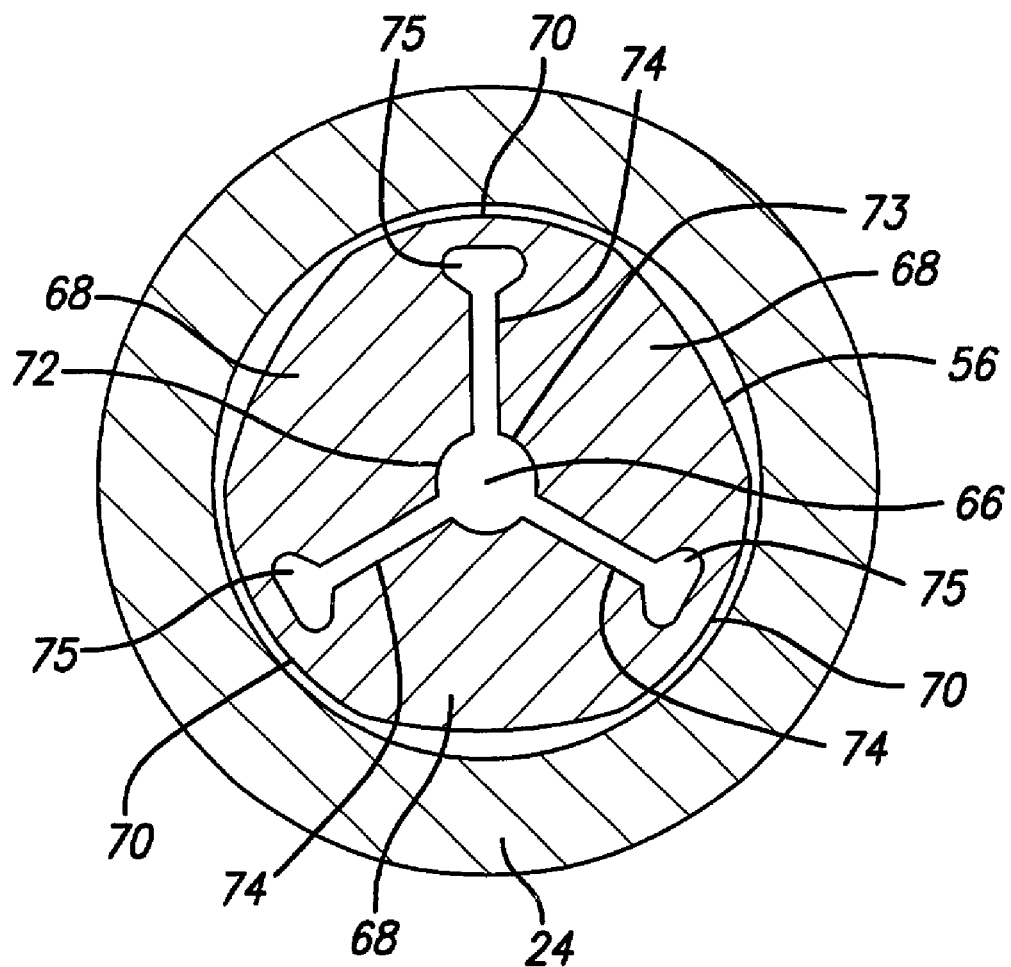
FIG. 9 is a sectional view of the medical connector of FIG. 7, taken across the line marked 9—9 showing the expandable section in its self-collapsed configuration.

Referring to FIG. 9, the expandable section 56 is shown in its relaxed configuration. That is, the material of the expandable section 56 is configured so that absent any external forces, the inner conduit 66 appears as shown in FIG. 9. The inner conduit 66 appears as a solid piece of material with a center hub bore, three cuts, and strain reliefs. The center circular bore 73 has three cuts 74 that radiate outward from the central bore 73, and at the end of each cut, a strain relief in the form of an enlarged slot 75 exists. Because the membranes 70 are located at the end of each of the cuts, stretching will occur at these points and will permit the expansion of the inner conduit 66, as is discussed and shown in greater detail below.

The cross-sectional view of FIG. 7 shows the interaction of the three parts of the connector of the embodiment discussed. The upper housing portion 24 includes the first port 28 that comprises a female Luer connector port with thread elements 30 located about the exterior, and is securely connected to the lower housing portion 26. The lower housing portion 26 includes the second port 32 that comprises the male Luer connector 34 with a threaded locking collar 36. The internal threads are visible in FIG. 7. The lower housing portion 26 also includes the flow post 40 integrally formed with the lower housing portion. In this embodiment, the flow post has a length that results in its location somewhat within the first housing portion 24 when the complete housing 22 has been assembled. This feature is also apparent from FIG. 2.

Figure 8:
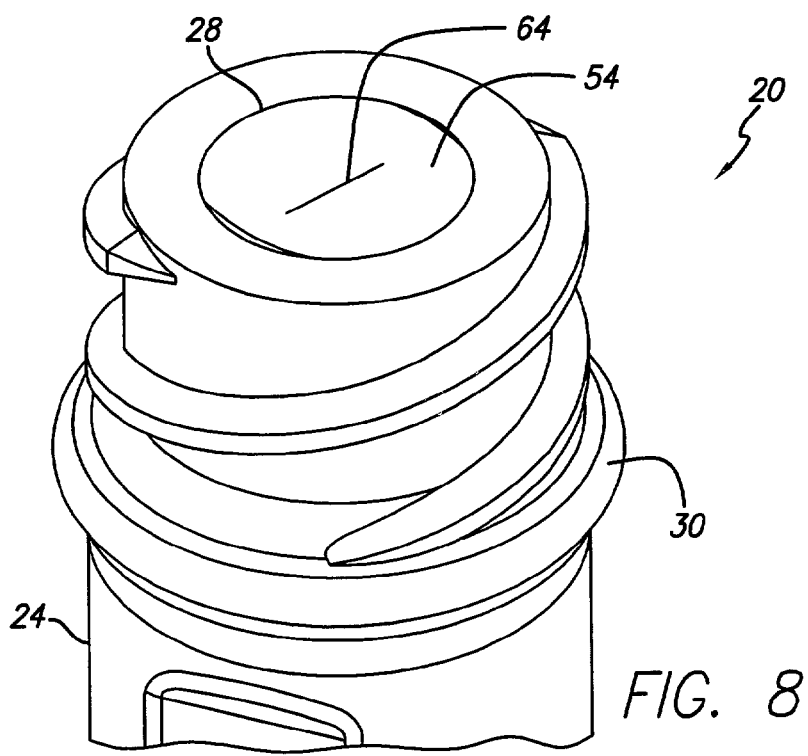
FIG. 8 is an enlarged perspective view of the first port of the connector of FIG. 1 showing the self-opening head of the piston element in the first position with the marquise shaped bore closed to fluid flow.

Further, the movable element or piston 38 is shown mounted over the flow post and extending to the first port 28 of the upper housing portion 24. The piston head 54 is within the narrowed Luer taper region 100 of the first housing portion and this narrowing has caused a compressive force to be exerted against the elliptical portion 60 of the piston head 54, thereby causing the marquise-shaped bore 64 to be closed. This closed configuration is more clearly shown in FIG. 8 where the top of the piston head can be seen and the closed bore 64 is clearly seen. It should also be noted that this configuration permits easy wiping of the piston head before use. This closed bore 64 blocks the fluid flow through the valve 20 in this unaccessed state.

It should be noted that the fluid volume within the connector 20 in this unaccessed state is defined by the open portion in the piston head under the closed bore 64, the inner conduit 66 through the expandable section, the lumen 42 of the flow post and the second port 32. It is also informative to note that the flow post and second port are rigid structures and their internal volumes do not change with the connector being accessed, as will be discussed below. While the bore 64 of the piston head may appear to be open in FIG. 7, it is closed. The particular orientation of the cross section in FIG. 7 results in the marquise-shaped bore being shown along its length, and thus has the appearance of being open. However, a perspective view of the top of the piston head, such as that shown in FIG. 8, demonstrates that the bore is closed.

In further reference to FIG. 7, the spring 58 includes a base 114 that is mounted at the base 116 of the flow post 40. The spring may be held in place at the base of the flow post by friction, adhesive, or other means. Reference may be made to incorporated U.S. Pat. No. 5,676,346 to Leinsing for further details. Extending proximally from the center of the base 116 is the flow post 40. Extending distally from the base is the male-Luer taper connector 34 having a lumen 35 that is coaxial with the lumen 42 of the flow post 40.

Turning now to FIG. 10, the connector 20 in an accessed state is shown. A blunt cannula 130, which is a male Luer connector in this case, has been inserted into the first port 28 into contact with the top section 60 of the piston element head and has moved the piston element so that the expandable section 56 is now partially over the flow post 40. The spring 58 is now compressed.

As is described in U.S. Pat. No. 5,676,346 to Leinsing, the configuration of the piston head results in the bore 64 of the piston head being self-opening. That is, the bore 64 is normally open and radial compressive forces must be applied to the piston head to close the bore. Thus, when the male cannula 130 presses the piston head into the larger interior of the housing 22 and radial compressive forces are removed from the piston head, the bore 64 self-opens to now permit fluid flow through the connector 20. The elliptical-conical section 61 shown in FIGS. 3 and 4 also uses the axial force from insertion of the male Luer 130 to facilitate the opening of the bore 64. This is also called the "coin purse" effect.

In the presently described embodiment, the expandable section 56 is configured so that the inner conduit 66 is urged to expand by being forced over the flow post 40. That is, the inner conduit 66 is normally at its first collapsed width and expansive radial forces must be applied to the expandable section to expand the inner conduit, or to force it to have its larger second width or diameter. Thus, when the male cannula 130 presses the piston head into the larger interior of the housing 22, and expansive radial forces are applied to the expandable section by the flow post 40, the inner conduit 66 expands to its larger second width that will now permit a larger fluid volume within the fluid passageway of the connector 20. This larger width either exactly compensates for the decrease in length of the fluid passageway through the connector or adds additional volume to the fluid passageway. As can be seen by reference to FIG. 10, pressing the male cannula 130 into the connector 20 shortens the length of the fluid passageway through the connector from the length in FIG. 7 and would otherwise thereby reduce the volume of the fluid flow path also. However, the increased width of the inner conduit volumetrically counteracts this decrease in length. This is discussed in more detail below in regard to FIGS. 14 and 15.

In FIG. 10, it is shown that the expandable section 56 and the inner conduit 66 are now located partially over the flow post 40. This arrangement can be seen in greater detail in the enlarged diagram of FIG. 12. The flow post however includes a lumen 42 through which fluid may flow and a longitudinal slot 46 in the wall 44 of the flow post through which fluid may continuously flow into and out of the flow post lumen and into and out of the inner conduit as shown in FIG. 10. Fluid that may reach the spring section will also flow into or out of the slot of the flow post so that continuous flow occurs throughout the connector when in the accessed state. No reservoirs or dead space of any nature exist so that each part of the fluid passageway is adapted for continuous flow through it.

Figure 11:
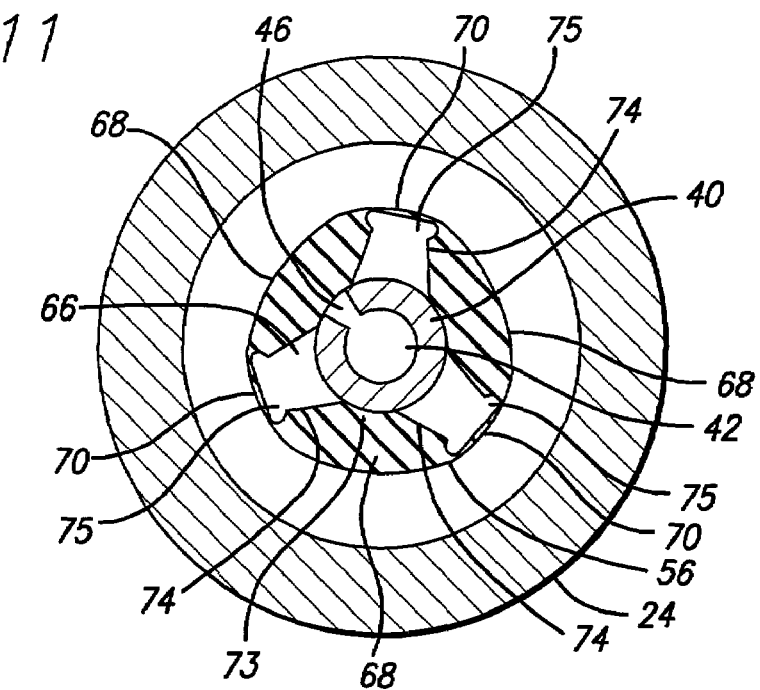
FIG. 11 is a sectional view of the medical connector of FIG. 10 taken across line 11—11 showing the inner conduit of the expandable section at its second width for increased internal volume.
Figure 12:
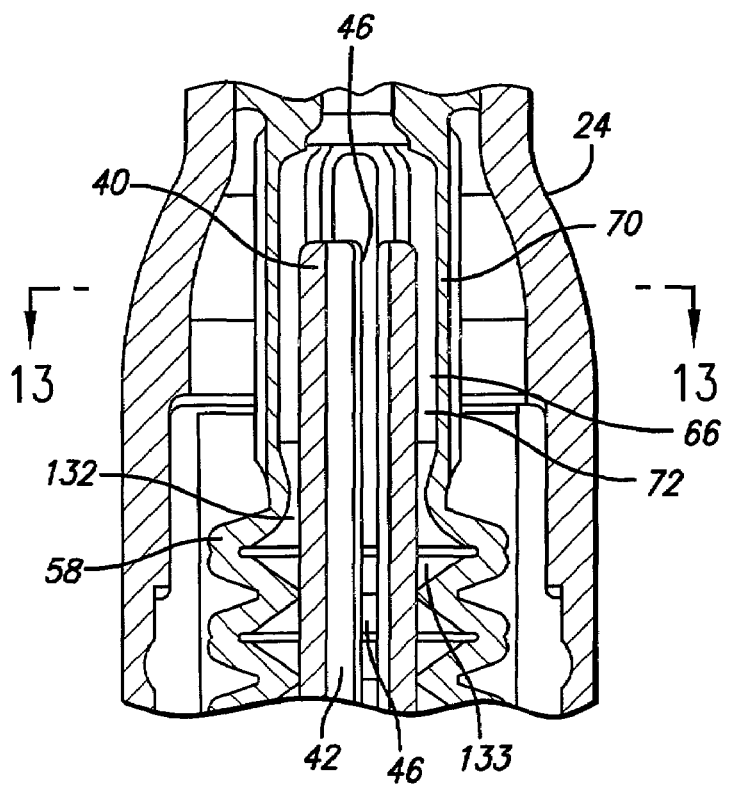
FIG. 12 is a detail view of the portion of FIG. 10 showing in enlarged detail the interaction of the slot and lumen in the flow post with the inner conduit of the expandable section, and the action of the spring section on the expandable section.

Turning now also to FIG. 11 in conjunction with FIG. 10, the interaction of the flow post 40, its lumen 42, and its slot 46 with the inner conduit 66 may be seen from another angle. FIG. 11 is a cross sectional view of FIG. 10, which is a connector in the accessed state. In FIG. 11, a possible orientation of the slot of the flow post with the inner conduit wall is shown. In this configuration, the slot 46 of the flow post resides against one of the stiff walls 68 of the inner conduit. This particular positioning does not prevent fluid flow through the inner conduit because orifices 132 are provided at the bottom of the inner conduit to provide for fluid flow between the inner conduit and the distal portion of the spring section. The enlarged diagrams of FIGS. 12 and 13 show the orifices 132 more clearly. In the accessed state, the point of connection between the spring section 58 and the expandable section 56 may be configured to define the orifices 132 through which the flow post 40 protrudes. Thus, at the proximal end of the inner conduit 66, a plurality of gaps or orifices 132 may be defined between the piston element 38 and the flow post 40 which collectively provide a fluid flow path between all portions of the inner conduit 66 and the distal section 133 (see FIG. 12) of the spring section 58, from whence fluid may flow into the lumen 42 of the flow post via the slot 46.

Thus, the expandable section 56 is configured so that when the connector 20 is accessed by a blunt cannula 130, fluid may flow continuously through the entire inner conduit 66 without a reservoir being developed at any point in which fluid may be trapped, held, or retained. The piston element 38 is configured to provide a larger fluid passageway width at the location of the expandable section 56 when the connector is in the accessed state, as shown in FIG. 10, thus increasing the volume of the fluid passageway or keeping it the same as the volume of the fluid passageway in the unaccessed state, as shown in FIG. 7.

It will be appreciated that, when the slot 46 of the flow post is oriented so that it is facing one of the membrane elements 70 in FIG. 11, fluid may flow directly between the lumen 42 of the flow post and the inner conduit 66 via the slot 46 or in parallel with fluid flow through the orifices 132.

To briefly reiterate, in the accessed state as shown in FIG. 10, the internal fluid passageway through the connector 20 is through the bore of the piston element, through the head of the piston element, through the entire inner conduit 66, through the lumen 42 of the flow post, and through the second port 32. It will be appreciated that flow may be reversed when fluid is withdrawn through the connector. It should be noted that in comparison to FIG. 7, the internal fluid passageway of FIG. 10 has been shortened by the amount that the blunt cannula 130 has entered the first port 28, or, put another way, the amount by which the inner conduit 66 now covers the flow post 40. However, the expansion of the inner conduit to a greater width has volumetrically compensated for the decrease in length of the internal fluid passageway. Conversely, as the blunt male connector 130 is withdrawn from the first port 28, the internal fluid passageway through the connector will lengthen, but at the same time the width of the inner conduit will decrease. If the decrease in width decreases the volume of fluid in the internal fluid passageway of the connector by an amount greater than the increase in length causes an increase in volume, a bolus of fluid may be expelled by the connector 20 through the second port 32.

In further detail, the inner conduit will be discussed. Referring to FIG. 13, the membrane elements 70 may be adapted to stretch when a radially expansive force is applied to the expandable section, and will allow the wall elements 68 to move apart from each other, thus increasing the width or diameter of the inner conduit 66. The flow post 40 has entered the central bore 73 and because the flow post is larger than the central bore, that bore 73 has been enlarged. Along with the enlargement of the central bore 73, the slots 74 have also opened to allow greater volume for the conduction of fluid. Further, the strain relief slots 75 have also expanded to permit a greater volume in the inner conduit 66. The strain relief slots 75 and the surrounding membranes 70 also act as hinges that permit the enlargement of the inner conduit 66 upon insertion of the flow post 40 therein. Due to the relative stiffness of the wall elements 68, the length 134 of the inner conduit 66 remains substantially constant under such radially expansive force. Where the radially expansive force is removed or reduced, the inner conduit 66 will be urged to collapse to the smaller first width under the force provided by the resilient material of the expandable section 56.

Figure 16:
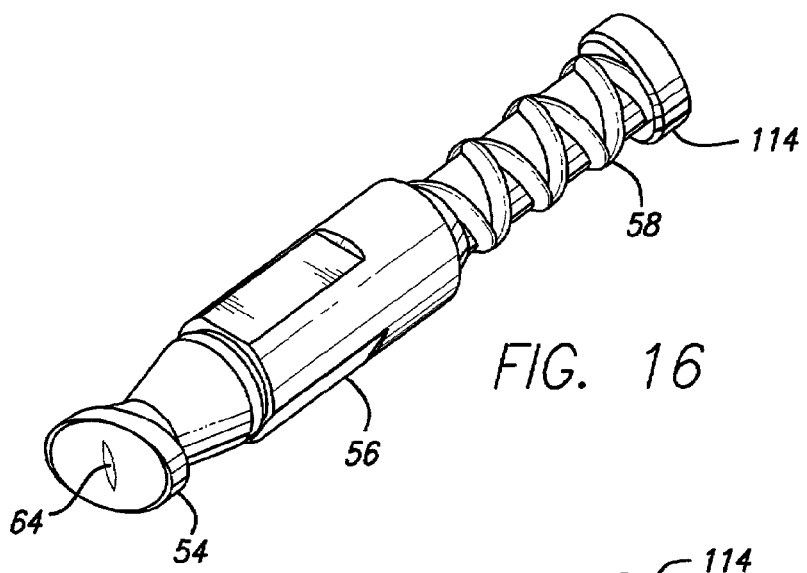
FIGS. 16 through 18 are perspective views of the piston element showing alternative configurations of the spring section.
Figure 17:
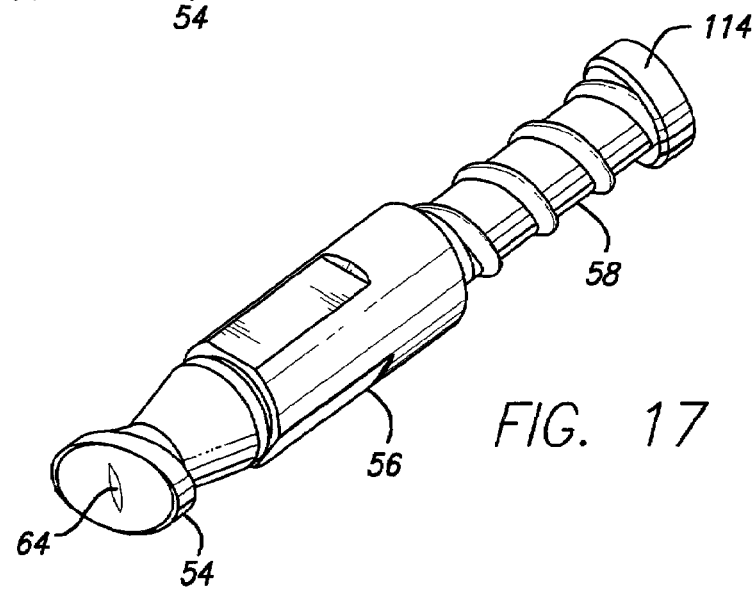
Figure 18:
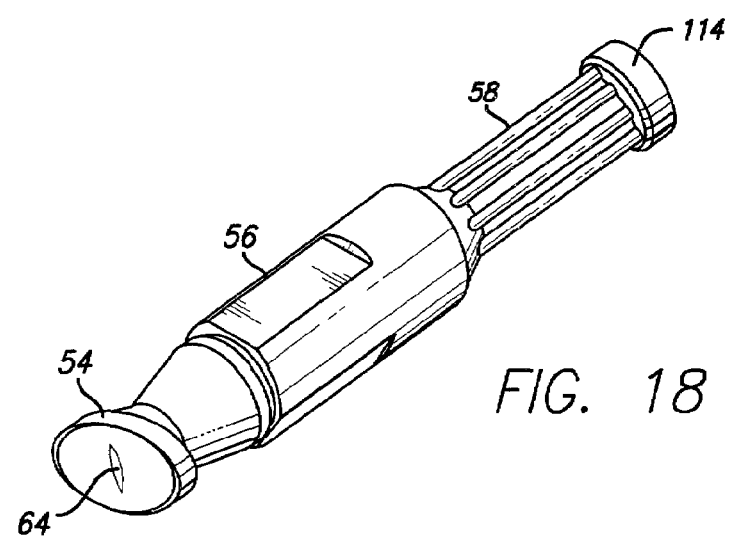

In regard to the spring section 58, the piston element 38 resiliently deforms so as to permit the annular portions 110 to alternatingly deform inwardly and outwardly, while allowing rotation to occur mainly at the hinges 112, as exemplified in FIG. 10. It will be appreciated that modifications in the shapes of the spring section are possible. Changes may be made to affect flow rate, restoring force, spring section return rate, differential bolus volume, sealing, Luer retention, piston retention, and acceptance of blunt cannulas. Modifications include changing the number of annular sections, wall thickness and height, or may include different configurations of the spring section entirely, as exemplified in FIGS. 16–18.

In the embodiment shown, the spring section 58 also contributes to the bolus effect. The spring section includes a bore that forms a part of the connector internal fluid passageway. That spring section bore has a first volume when the spring section is uncompressed and a second volume when the spring section is compressed. The spring section bore second volume is greater than the spring section bore first volume. Thus when the spring is placed in the compressed configuration shown in FIG. 10, the internal volume of the spring section 58 actually increases somewhat over the internal volume of the spring section in its uncompressed configuration, as shown in FIG. 7. Therefore, as the male cannula 130 is withdrawn from the port 28, the spring section 58 will return to its uncompressed, lower internal volume and the fluid differential will be expelled in the distal direction.

FIGS. 14 and 15 are schematic drawings that present the concept of the adjustment of the volume of the internal fluid passageway through a connector based on expansion and contraction of a part of that passageway. In FIG. 14, a schematic connector 136 is shown that includes an internal fluid passageway 138 having a length 140 linking a first port 142 with a second port 144. In FIG. 14, the single dashed line adjacent the first sport 142 is used to indicate the closed bore of the piston head. Forming part of the fluid passageway 138 is an inner conduit 146 having a first width 148. In FIG. 15, a blunt cannula 150 has been inserted into the first port 142 of the connector 136 and has shortened the internal fluid passageway 138 which now has a length shown by numeral 154. The difference between the length 140 of the internal fluid passageway in FIG. 14 and the length 154 of the internal fluid passageway in FIG. 15 is shown by numeral 156. If nothing else were to change, the volume of the internal fluid passageway 138 of FIG. 15 would now be less than that of FIG. 14, and a negative bolus effect could be expected upon removal of the male cannula 150. However, the width 160 of the inner conduit 146 in FIG. 15 has been expanded to be greater than the width 148 of the inner conduit of FIG. 14. It will be appreciated that, by appropriate selection of the expanded and compressed widths of the inner conduit, the volume of the fluid path 138 can be made to increase, stay the same, or decrease when a blunt cannula is made to access the connector 136. Where the volume increases, a positive bolus-effect is created when the cannula is removed from the connector. Where the volume remains the same, a neutral-bolus effect is created, and, where the volume decreases, a negative-bolus effect is created.

Turning now to the operation of the medical connector 20, the connector is initially in its unaccessed state or closed position as shown in FIG. 7. The resiliency of the spring section 58 of the piston element 38 causes the piston head 54 to be biased into the narrowed Luer taper portion 100. The shoulder 62 of the piston head 54 contacts the tapered lock portion 104 of the upper housing portion 24 and controls the position of the top of the piston head 54 in relation to extending beyond the edge of the first port 28 thus forming a swabbable surface therewith. The sharp pointed ends of the marquise-shaped bore 64 facilitate a tight seal upon compression of the bore along its minor axis and by compression of the top section 60 of the piston head 54 along its major axis.

Just prior to accessing the connector with a male Luer connector at the first port 28, the top surface of the piston head 54 and the edge of the first port may be cleaned by, for example, passing a sterilizing swipe over the smooth surface of the piston head lying flush, slightly above, or slightly below the upper surface of the first port. The connector is then ready to be accessed by a standard male Luer connector with or without a threaded locking collar.

The tip of a male Luer connector is brought into contact with the proximal surface of the top section 60 of the piston head 54. The application of sufficient pressure causes the spring section 58 of the piston element 38 to axially contract and to compress in a bellows-like configuration so that orifices 132 are defined between the spring section 58 and the flow post 40. As the spring section 58 axially contracts, the piston head 54 moves out of the narrowed Luer taper portion 100 of the upper housing portion 24 and into the center portion 102. As the piston head 54 clears the tapered lock portion 104 and is moved into the center portion 102, the larger internal diameter of the center portion allows the top section 60 of the piston head to self-expand and to tend to assume its normal elliptical shape and the same action allows the bore 64 to tend to self-open to assume its normally open marquise-shape bore configuration thereby opening a fluid passageway through the connector and the piston head 54.

Further, as the spring section 58 contracts into a bellow shape under the axial pressure of the male Luer tip 130, the expandable section 56 moves in the distal direction from the constricted center portion 102 of the upper housing 24 into the larger diameter bottom portion 106 of the upper housing, at the same time forcing the inner conduit 66 over the flow post 40, thus causing the inner conduit 66 to expand.

As the blunt cannula 130 becomes fully inserted in the connector 20, the expandable section fully expands, thereby expanding the width 72 of the inner conduit 66. Flow may now occur through the connector. The internal fluid passageway through the connector has expanded in width to volumetrically compensate for the decrease in length, and fluid flows continuously through every part of the internal fluid passageway of the connector. Additionally, fluid flows through the entire expandable section 56 due to the slot 46 in the wall 44 of the flow post 40 and the orifices 132 that permit fluid flow through the distal end of the inner conduit 66 into the proximal section 133 of the spring section and into the slot 46.

When the blunt cannula 130 is withdrawn from the connector 20 to allow the connector to return to the non-accessed state, the restoring force generated by the spring section 58 of the piston element 38 causes the expandable section 56 to be urged off the flow post 40, proximally past the ramp section 108, and into the constricted confines of the center section 102 of the upper housing portion 24. As the inner conduit 66 leaves the flow post 40, it self-collapses where the inner width 72 of the inner conduit decreases to its first width, as shown in FIG. 7. Thus, the volume of the fluid passageway through the conduit may decrease, depending on the selected dimensions of the expandable section 56 and its inner conduit 66. If so, a bolus of fluid that was within the inner conduit will be expelled through the second port 32. Simultaneously, the elliptical top portion 60 of the piston head 54 is guided by the tapered lock section 104 into the Luer taper section 100 where it is once again urged into a narrowed circular shape to close off the orifice 64 and reestablish a positive seal against the fluid flow passageway through the connector 20.

Thus there has been shown and described a new and useful valve for use in medical connectors that provides a controllable bolus effect. Depending on the expanded and compressed widths selected for the inner conduit 66 of the expandable section in relation to the configuration of the balance of the piston element 38, a positive-bolus, neutral-bolus, or negative-bolus effect can be achieved as the connector is placed in an unaccessed state from an accessed state.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A connector for controlling the flow of fluid, the connector having an internal fluid passageway by which fluid may flow through the connector, the connector comprising:
   a housing having a first port and a second port, the first port being adapted to receive a blunt cannula and the second port adapted for fluid communication with a fluid conduit;
   a movable element positioned within the housing, the movable element having a first position at which the movable element blocks fluid flow through the housing and a second position at which the movable element permits fluid flow through the housing, the movable element comprising a head and an expandable section, the head defining a self-opening bore forming a part of the fluid passageway, the head configured such that when the movable element is in the second position, the bore self-opens to permit fluid flow, the self-opening bore adapted to close when the movable element is in the first position, the expandable section defining an inner conduit, the inner conduit forming a part of the fluid passageway through the connector, the inner conduit having a center hub bore disposed centrally within the expandable section and a plurality of radial slots radiating outwardly from the center hub bore, the expandable section configured to self-collapse such that the inner conduit has a first width; and
   a flow post that is disposed within the housing, the flow post being larger than the center hub bore, the flow post adapted so that when the movable element is at the first position, the flow post does not extend into the center hub bore, and when the movable element is at the second position, the flow post extends into the center hub bore and expands the center hub bore and the radial slots so as to force the inner conduit to have a second width, the second width being larger than the first width;
   wherein the inner conduit of the expandable section is configured such that fluid may continuously flow through the entire inner conduit including the center hub bore and the radial slots when the movable element is in the second position.

2. The connector of claim 1 wherein the first and second widths of the inner conduit of the expandable section are selected such that the fluid passageway has a first volume when the movable element is in the first position and a second volume when the movable element is in the second position, the second volume being larger than the first volume.

3. The connector of claim 1 wherein the first and second widths of the inner conduit of the expandable section are selected such that the fluid passageway has a first volume when the movable element is in the first position and a second volume when the movable element is in the second position, the second volume being approximately the same as the first volume.

4. The connector of claim 1 wherein the flow post having opposing ends, the flow post defining a lumen extending between the opposing ends, one end being in fluid communication with the second port and the lumen forming a part of the internal fluid passageway through the connector.

5. The connector of claim 4 wherein the flow post comprises a wall, the wall defining a slot providing a fluid path between the exterior of the tube and the lumen.

6. The connector of claim 5, wherein the flow post is configured in relation to the moveable element such that, when the movable element is in the second position, the lumen and slot of the flow post are positioned, at least in part, within the inner conduit of the expandable section such that fluid may flow through the inner conduit of the expandable section, through the slot, through the lumen of the flow post, and through the second port of the housing.

7. The connector of claim 6 wherein:
   the inner conduit of the expandable section has opposing first and second ends, the first end being adjacent the self-opening bore of the head; and
   the movable element defines an orifice located at the second end of the inner conduit, the orifice forming part of a flow path extending from the self-opening bore, through the inner conduit, and out of the inner conduit through the orifice.

8. The connector of claim 7 wherein:

the lumen and slot of the flow post extend, at least in part, to a location outside the inner conduit of the expandable section when the movable element is at the second position; and said flow path further extends from the orifice, through the slot, and into the lumen at the location outside of the inner conduit.

9. The connector of claim 7 wherein:

the moveable element further comprises a spring section connected to the expandable section; and said flow path further extends from the orifice, and into the spring section.

10. The connector of claim 1 wherein the housing includes a narrowed region adjacent the first port, the head of the movable element being located in the narrowed region when the movable element is in the first position, the narrowed region being dimensioned so as to cause the self-opening bore of the head to close.

11. The connector of claim 1 wherein the housing includes a constricted region, the expandable section being located in the constricted region when the movable element is in the first position, the constricted region being dimensioned so as to receive the expandable section to permit the inner conduit to move to the first width.

12. The connector of claim 11 wherein:

the expandable section is connected to the head; and the moveable element further comprises a spring section connected to the expandable section, the spring section being adapted to urge the movable element to the first position at which the expandable section is placed within the constricted region.

13. The connector of claim 12 wherein:

the spring section includes a bore that forms a part of the connector internal fluid passageway;

the spring section bore has a first volume when the spring section is uncompressed and a second volume when the spring section is compressed;

wherein the spring section bore second volume is greater than the spring section bore first volume.

14. The connector of claim 12 wherein the head, and the expandable section, and the spring section are molded as an integral moveable element.

15. The connector of claim 1 wherein the expandable section comprises a plurality of relatively flexible membrane elements and a plurality of relatively stiff wall elements, the membrane elements connecting together adjacent edges of the wall elements.

16. The connector of claim 15 wherein the membrane elements are adapted to stretch to permit expansion of the inner conduit when the inner conduit has the second width.

17. The connector of claim 1 wherein at least one of the first port, the second port, and the movable element is formed to include an antimicrobial agent.

18. The connector of claim 17 wherein the antimicrobial agent is chosen from materials consisting of silver, chlorhexidine PHMB, silver oxide, and silver sulfadiazine.

19. A connector for controlling the flow of fluid, the connector having an internal fluid passageway by which fluid may flow through the connector, the connector comprising:

a housing having a first port and a second port, the first port being adapted to receive a blunt cannula and the second port adapted for fluid communication with a fluid conduit; and a movable element positioned within the housing, the movable element having a first position at which the movable element blocks fluid flow through the housing and a second position at which the movable element permits fluid flow through the housing, the movable element comprising a head and an expandable section, the head defining a self-opening bore forming a part of the fluid passageway, the head configured such that when the movable element is in the second position, the self-opening bore self-opens to permit fluid flow, the self-opening bore adapted to close when the movable element is in the first position, the expandable section defining an inner conduit, the inner conduit forming a part of the fluid passageway through the connector, the inner conduit having a center hub bore disposed centrally within the expandable section and a plurality of radial slots radiating outwardly from the center hub bore, the expandable section configured to self-collapse such that the inner conduit has a first width; and a flow post disposed within the housing, the flow post being larger than the center hub bore, the flow post adapted so that when the movable element is at the first position, the flow post does not extend into the center hub bore, and when the movable element is at the second position, the flow post extends into the center hub bore and expands the center hub bore and the radial slots so as to force the inner conduit to have a second width, the second width being larger than the first width;

wherein the first and second widths of the inner conduit of the expandable section are selected such that the fluid passageway has a first volume when the movable element is in the first position and a second volume when the movable element is in the second position, the second volume being at least the same or larger than the first volume and wherein the inner conduit being configured such that fluid may continuously flow through the entire inner conduit including the center hub bore and the radial slots when the movable element is located in the second position.

20. The connector of claim 19 wherein the second volume being larger than the first volume.

21. The connector of claim 19 wherein the second volume being approximately the same as the first volume.

22. The connector of claim 19 wherein the flow post having opposing ends, the flow post defining a lumen extending between the opposing ends, one end being in fluid communication with the second port and the lumen forming a part of the internal fluid passageway through the connector.

23. The connector of claim 22 wherein the flow post comprises a wall, the wall defining a slot providing a fluid path between the exterior of the tube and the lumen.

24. The connector of claim 23 wherein the flow post is configured in relation to the moveable element such that, when the movable element is in the second position, the lumen and slot of the flow post are positioned, at least in part, within the inner conduit of the expandable section such that fluid may flow through the inner conduit of the expandable section, through the slot, through the lumen of the flow post, and through the second port of the housing.

25. The connector of claim 24 wherein:
the inner conduit of the expandable section has opposing first and second ends, the first end being adjacent the self-opening bore of the head; and
the movable element defines an orifice located at the second end of the inner conduit, the orifice forming part of a flow path extending from the self-opening bore, through the inner conduit, and out of the inner conduit through the orifice.

26. The connector of claim 25 wherein:
the lumen and slot of the flow post extend, at least in part, to a location outside the inner conduit of the expandable section when the movable element is at the second position; and
said flow path further extends from the orifice, through the slot, and into the lumen at the location outside of the inner conduit.

27. The connector of claim 26 wherein:
the moveable element further comprises a spring section defining a bore, the spring section being connected to the expandable section; and
said flow path further extends from the orifice, into the bore of the spring section.

28. The connector of claim 27 wherein:
the bore of the spring section has a first volume when the spring section is uncompressed and a second volume when the spring section is compressed;
wherein the spring section bore second volume is greater than the spring section bore first volume.

29. The connector of claim 19 wherein the housing includes a narrowed region adjacent the first port, the head of the movable element being located in the narrowed region when the movable element is in the first position, the narrowed region being dimensioned so as to cause the self-opening bore of the head to close.

30. The connector of claim 19 wherein the housing includes a constricted region, the expandable section being located in the constricted region when the movable element is in the first position, the constricted region being dimensioned so as to cause the width of inner conduit of the expandable section to move to the first width.

31. The connector of claim 30 wherein:
the expandable section is connected to the head; and
the moveable element further comprises a spring section connected to the expandable section, the spring section being adapted to urge the movable element to the first position at which the expandable section is placed within the constricted region, the constricted region being dimensioned so as to receive the expandable section to permit the inner conduit to move to the first width.

32. The connector of claim 31 wherein the head, and the expandable section, and the spring section are molded as an integral moveable element.

33. The connector of claim 19 wherein at least one of the first port, the second port, and the movable element is formed to include an antimicrobial agent.

34. The connector of claim 33 wherein the antimicrobial agent is chosen from materials consisting of silver, chlorhexidine PHMB, silver oxide, and silver sulfadiazine.

35. The connector of claim 19 wherein the expandable section comprises a plurality of flexible membrane elements and a plurality of relatively inflexible wall elements, the membrane elements connecting together adjacent edges of the wall elements.

36. The connector of claim 35 wherein the membrane elements are adapted to stretch to permit expansion of the inner conduit when the inner conduit has the second width.

37. A connector for controlling the flow of fluid, the connector having an internal fluid passageway by which fluid may flow through the connector, the connector comprising:
a housing having a first port and a second port, the first port being adapted to receive a blunt cannula and the second port adapted for fluid communication with a fluid conduit;
a movable element positioned within the housing, the movable element having a first position at which the movable element blocks fluid flow through the housing and a second position at which the movable element permits fluid flow through the housing, the movable element comprising a head and an expandable section, the head defining a self-opening bore forming a part of the fluid passageway, the head configured such that when the movable element is in the second position, the self-opening bore moves to its normally open configuration to permit fluid flow, the self-opening bore adapted to close when the movable element is in the first position, the expandable section defining an inner conduit, the inner conduit forming a part of the fluid passageway through the connector, the inner conduit having a center hub bore disposed centrally within the expandable section and a plurality of radial slots radiating outwardly from the center hub bore, the expandable section configured to self-collapse such that the inner conduit has a first width and
a flow post comprising a first end, a second end in fluid communication with the second port, a wall that defines a lumen forming a part of the internal fluid passageway through the connector, and a longitudinal slot formed through the wall and into communication with the lumen whereby fluid may flow into and out of the lumen through the longitudinal slot, the flow post being larger than the center hub bore;
wherein the flow post is disposed within the housing and adapted so that when the movable element is at the second position, the flow post extends into the center hub bore and expands the center hub bore and the radial slots so as to force the inner conduit to have a second width, the second width being larger than the first width;
wherein the inner conduit being configured such that fluid may continuously flow through the entire inner conduit including the center hub bore and the radial slots when the movable element is located in the second position; and
wherein the lumen and slot of the flow post are located within the inner conduit of the expandable section when the movable element is in the second position whereby fluid may flow through the inner conduit of the expandable section, through the slot, through the lumen of the flow post, and through the second port of the housing.

38. The connector of claim 37 wherein:
the inner conduit of the expandable section has a first end and a second end; and
the movable element also comprises an orifice located at the second end of the inner conduit that provides a flow path between the inner conduit and a location of the fluid passageway that is outside of the inner conduit.

39. The connector of claim 38 wherein:
the lumen and slot of the flow post extend to a location outside the inner conduit of the expandable section when the movable element is at the second position; and
the orifice provides a flow path between the inner conduit and the slot and the lumen of the flow post at the location outside of the inner conduit.

40. The connector of claim 39 wherein:
the moveable element further comprises a spring section connected to the expandable section, the spring section located over the lumen and slot of the flow post that extend to the location outside the inner conduit; and
the orifice provides the flow path through the spring section.

41. The connector of claim 37 further comprising a narrowed region adjacent the first port of the housing at which the head of the movable element is located when the movable element is in the first position, the size of the narrowed region selected so as to cause the self-opening bore of the head to close to prevent fluid flow through the fluid passageway of the connector.

42. The connector of claim 37 further comprising a constricted region adjacent the first port of the housing at which the expandable section is located when the movable element is in the first position, the size of the constricted region selected so as to allow the inner conduit of the expandable section to return to its second width.

43. The connector of claim 42 wherein:
the expandable section is connected to the head; and
the moveable element further comprises a spring section connected to the expandable section, the spring section being adapted to urge the movable element to the first position at which the head is placed within the narrowed region.

44. The connector of claim 43 wherein:
the spring section includes a bore that forms a part of the connector internal fluid passageway;
the spring section bore has a first volume when the spring section is uncompressed and a second volume when the spring section is compressed;
wherein the spring section bore second volume is greater than the spring section bore first volume.

45. The connector of claim 43 wherein the head, and the expandable section, and the spring section are molded as an integral element from a resilient material.

46. The connector of claim 37 wherein the expandable section comprises a plurality of substantially inflexible wall elements and a plurality of substantially flexible membrane elements, the membrane elements connecting together adjacent edges of the wall elements.

47. The connector of claim 46 wherein the membrane elements are adapted to stretch to permit expansion of the inner conduit when the inner conduit has the second width.

48. The connector of claim 37 wherein at least one of the first port, the second port, and the movable element is formed to include an antimicrobial agent.

49. The connector of claim 48 wherein the antimicrobial agent is chosen from materials consisting of silver, chlorhexidine PHMB, silver oxide, and silver sulfadiazine.

50. A method for controlling the flow of fluid when inserting a blunt cannula in a first port of a conector housing to establish fluid communication with the housing, the method comprising:
moving a movable element that is positioned within the housing from a first position to a second position over a flow post, the movable element comprising a head with a self-opening bore that is closed to prevent fluid flow through the housing when the movable element is in the first position and is open when the movable element is in the second position to permit fluid flow, an expandable section defining an inner conduit and configured to self collapse such that the inner conduit has a first width;
moving a center hub bore of the inner conduit over the flow post, the flow post being larger than the center hub bore, including expanding the center hub bore and a plurality of radial slots extending radially from the center hub bore so as to force the inner conduit to have a second width larger than the first width;
causing fluid to flow continuously through the entire inner conduit including the center hub bore and the radial slots when the movable element is located at the second position.

51. The method of claim 50 wherein the step of expanding the center hub bore and the radial slots comprises increasing the volume for fluid flow through the connector.

52. The method of claim 50 wherein the step of expanding the center hub bore and the radial slots comprises maintaining the volume for fluid flow through the connector approximately constant.

53. The method of claim 50 wherein:
the step of moving the center hub bore over the flow post further includes moving the center hub bore over a lumen of the flow post forming a part of an internal fluid passageway through the connector; and
the step of causing fluid to flow through the entire inner conduit comprises causing fluid to flow through the lumen of the flow post also.

54. The method of claim 50 further comprising urging the movable element to the first position so that the self-opening bore is closed and the inner conduit returns to the first width.

* * * * *